United States Patent [19]

Downing, Jr.

[11] Patent Number: 4,841,157

[45] Date of Patent: Jun. 20, 1989

[54] OPTICAL BACKSCATTER TURBIDIMETER SENSOR

[76] Inventor: John P. Downing, Jr., 2428 39th Street, N.W., Washington, D.C. 20007

[21] Appl. No.: 141,268

[22] Filed: Jan. 6, 1988

[51] Int. Cl.[4] .................. G01N 15/07; G01N 21/49
[52] U.S. Cl. .................................... 250/574; 356/342
[58] Field of Search ............ 250/576, 578, 574, 575, 250/577, 573; 356/336, 342, 343, 338

[56] References Cited

U.S. PATENT DOCUMENTS

| | | | |
|---|---|---|---|
| 3,586,862 | 6/1971 | Topol | 250/218 |
| 3,617,757 | 11/1971 | Burr et al. | 250/218 |
| 3,640,626 | 2/1972 | Liskowitz | 356/103 |
| 3,665,201 | 5/1972 | Shea et al. | 250/218 |
| 3,714,444 | 1/1973 | Carr et al. | 250/218 |
| 3,721,500 | 2/1973 | Fugitt | 356/118 |
| 3,892,485 | 7/1975 | Merritt et al. | 356/103 |
| 4,006,988 | 2/1977 | Tamm | 356/4 |
| 4,017,186 | 4/1977 | Shofner et al. | 356/103 |
| 4,241,282 | 12/1980 | Tresch et al. | 250/574 |
| 4,260,258 | 4/1981 | Rose et al. | 250/573 |
| 4,361,403 | 11/1982 | Loos | 356/336 |
| 4,457,624 | 7/1984 | Goldberg et al. | 356/336 |

OTHER PUBLICATIONS

Downing, "An Optical Instrument for Monitoring Suspended Particulate in Ocean and Laboratory", *Proceedings Oceans '83 IEEE*, Sep. 1, 1983.
OBS-2 brochure, Downing & Associates.
OBS—3 brochure, Downing & Associates.
OBS-4 brochure, Downing & Associates, with Drawings "85-03" and 85-01 and FIGS. A & B.

*Primary Examiner*—David C. Nelms
*Assistant Examiner*—William L. Oen
*Attorney, Agent, or Firm*—Bernard, Rothwell & Brown

[57] ABSTRACT

There is disclosed a turbidimeter with an optical sensor having an IRED surrounded by four radiation detecting solar cells mounted on a printed circuit board which is encapsulated by a transparent potting material in a cavity of a housing. Additionally, the printed circuit board has a temperature sensor mounted thereon which is utilized by a sensor operating circuit to control the magnitude of the diode energizing current to compensate for variations in component response due to temperature variations.

13 Claims, 4 Drawing Sheets

OPTICAL BACKSCATTER TURBIDIMETER SENSOR

BACKGROUND OF THE INVENTION

1. Field of the Invention

The present invention relates to turbidimeters, and more particularly to apparatus for detecting particle concentrations in fluids using reflected radiation, such as infrared radiation.

2. Description of the Prior Art

The prior art contains optical sensors and submersible electronics units employed for measuring particle concentration in oceans, rivers, laboratories, or industrial applications. One type of prior art optical sensor has an infrared emitting diode (IRED) which generates infrared radiation with a peak radiant intensity at 950 nm, and includes radiation sensing cells such as solar cells for detecting the amount of infrared radiation reflected, or backscattered through angles from 110° to 165°, by particles. A WRATTEN filter with transmittances of 0.55 percent at optical wavelengths less than 790 nm and 83.2 percent at optical (infrared) wavelengths above 950 nm, is superimposed over the sensing cells to eliminate visible radiation while permitting infrared radiation to pass to the sensing cells. Infrared radiation is partially absorbed by fluids such as water to thus limit the measurement volume (typically 3 cc) and render the sensor insensitive to reflective surfaces and infrared sources outside the measurement volume. Additionally, infrared radiation is weakly reflected from gas bubbles and translucent biogenic material such as phytoplankton at large backscatter angles. The infrared emitter is energized with an alternating current signal, such as a 1.024 kHz square wave signal, and the detecting circuitry employs a synchronous detector to detect the magnitude of the alternating signal in the reflected radiation to eliminate sensing of background radiation.

The prior art turbidimeter sensors are generally characterized by one or mor deficiencies such as being excessively expensive and costly to produce, being subject to corrosion and failure, having insufficient range and sensitivity to detect a wide range of particle concentrations, being subject to variation due to temperature variation of the fluid being tested, being responsive to radiation scattered at smaller angles, being subject to component drift, being relatively non-linear in response, having excessive variations resulting from manufacture, etc.

SUMMARY OF THE INVENTION

In a first aspect, the invention is summarized in a turbidimeter sensor incorporating a printed circuit board upon which a radiation emitting diode together with a plurality of adjacent radiation detectors are mounted. The printed circuit board, diode, detectors and a baffle shielding the detectors from direct radiation from the diode are encapsulated in a transparent potting material in a cavity of a housing of the sensor.

In a second aspect, the invention is summarized in a turbidimeter sensor having a temperature sensor mounted in the sensor housing along with a radiation emitting diode and a plurality of radiation detectors. Sensor operating circuitry is adjusted by the output of the temperature sensor so that the turbidimeter is rendered relatively insensitive to changes in temperature of the fluid.

An object of the invention is to construct an optical sensor for detecting concentration of particles in a fluid with decreased production costs and improved sensitivity to reflected radiation.

One advantage of the invention is that employing a printed circuit board for mounting radiation emitting diodes and radiation sensors thereon in an optical sensor enables the efficient and less expensive production of the sensor while improving reliability due to more precise fixation of the emitter and detector positioning.

Another advantage of the invention is that a temperature sensing element mounted directly in an optical turbidity sensor enables adjustment of the operating signals so that temperature variations in the sensor output resulting from fluid temperature changes can be eliminated.

Still another advantage of the invention is that a radiation emitting diode with a plurality of radiation cells closely spaced to the diode results in limiting response to a relatively large minimum backscatter angle reducing the quantity of radiation reflected from bubbles and translucent biogenic material.

Features of the invention include a housing formed from glass-filled polycarbonate; an emitter, baffle and sensor arrangement resulting in a high sensing current output from radiation scattered by particles at large angles greater than about 140°; and a sensor which can ba efficiently and reliably mass produced using printed circuit boards, surface-mounting technology and injection molding processes.

Other objects, advantages, and features of the invention will be apparent from the following description of the preferred embodiments taken in conjunction with the accompanying drawings wherein:

DESCRIPTION OF THE PREFERRED EMBODIMENTS

Figure 1:
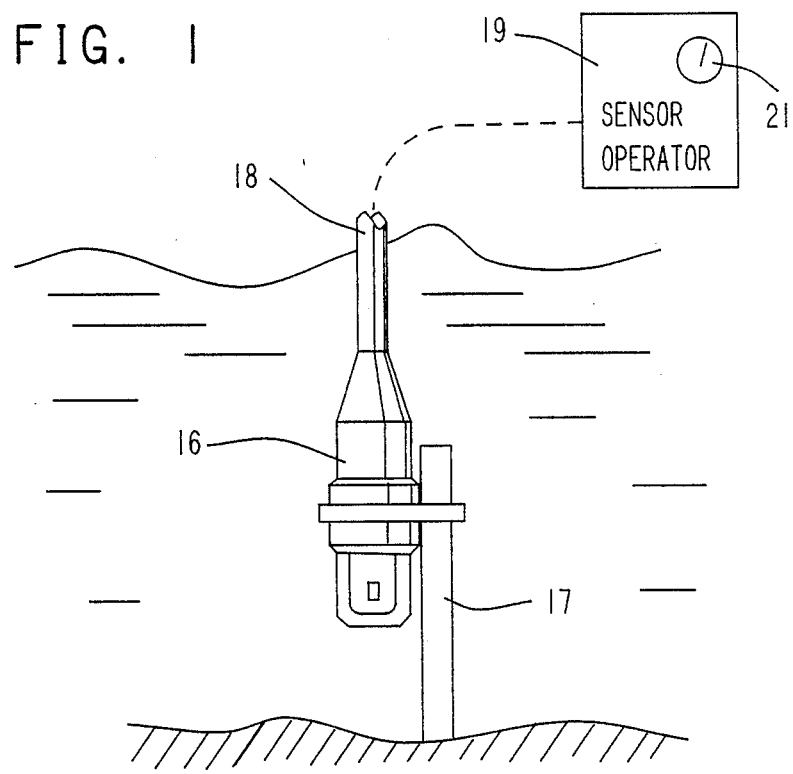
FIG. 1 is an elevation view, partially shown diagrammatically, of a turbidimeter with an optical sensor in accordance with the invention.

A turbidimeter, as shown in one possible deployment in FIG. 1, has a sensor 16 secured on a support 17 in a body of water and connected by a cable 18 to a sensor operator or instrumentation 19 which can include, for example, a meter 21 for indicating the turbidity, or concentration of particles in the water, in the region of the sensor 16. Alternatively, the instrumentation can include a recorder and/or can be contained in a sealed container suitably retained on the bottom of the body of water.

Figure 2:
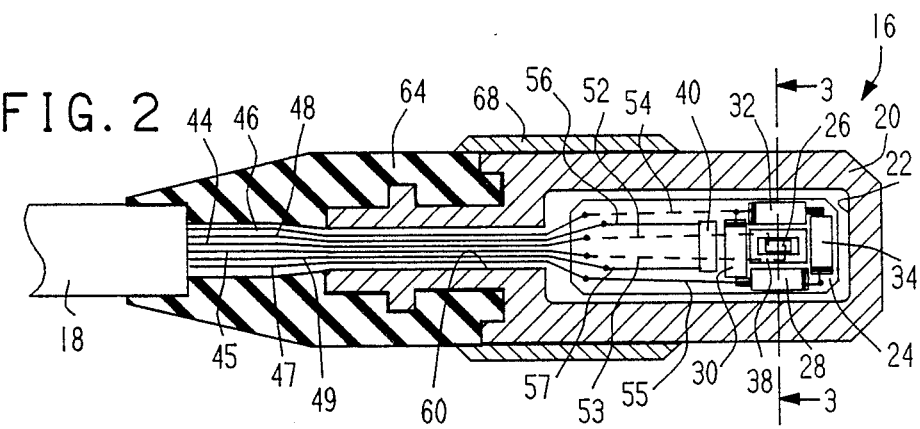
FIG. 2 is a sectional view of the sensor of FIG. 1.
Figure 3:
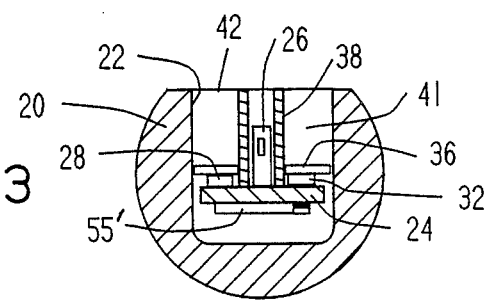
FIG. 3 is a section view taken at line 3—3 in FIG. 2.

As illustrated in FIGS. 2 and 3, the optical sensor 16 for the turbidimeter has a housing 20 with a cavity 22 containing a printed circuit board 24 on which are mounted a radiation emitting diode 26 and a plurality of radiation sensing cells 28, 30, 32 and 34. The radiation sensing cells 28, 30, 32 and 34 are arranged on four sides of the diode 26 adjacent thereto. An IR-opaque tubular baffle 38 separates the diode 26 from the sensing cells 28, 30, 32 and 34 so that radiation emitted by the diode 26 does not directly impinge upon the cells 28, 30, 32 and 34. A filter such as a WRATTEN filter 36 covers the sensors 32. Additionally, a temperature sensor 40 is mounted on the printed circuit board 24. The printed circuit board 24, diode 26, the sensors 28, 30, 32 and 34, the filter 36, the baffle 38 and the temperature sensor 40 are all encapsulated within a transparent potting material, such as optically clear epoxy 41, filling the cavity 22. The cavity 22 has an opening 42 through which the radiation emitter 26 can project and radiation sensors 28, 30, 32 and 34 can receive radiation to and from the fluid in the region in front of the opening 42 of the sensor. Electrical wires 44–49 in the cable 18 connect the printed circuit board to the electrical circuitry of FIG. 4 to operate the sensor.

The printed circuit board is contained within the cavity 22 so that its upper face is exposed to the opening 42 or so that it is generally perpendicular to a line passing through the middle of the opening 42 into the cavity 22. The radiation emitting diode 26 has its leads connected to bottom leads 52 and 53 of the PC board The leads 52 and 53 in turn are connected to the electrical wires 44 and 45. Upper electrodes of the radiation sensing cells 28, 30, 32 and 34 are connected by bottom lead 54 to the wire 46. The cells 28, 30, 32 and 34 are mounted by a conductive epoxy on the printed circuit board 24, this conductive epoxy also electrically connecting the bottom electrodes of the cells 28, 30, 32 and 34 to top lead 55 from line 47, and which is continued underneath at 55' the board 24 to the corner between cells 32 and 34. The temperature transducer 40 is surface mounted on top leads 56 and 57 of the printed circuit board and is connected by these leads to the lines 48 and 49.

The housing 20 is formed from a glass-filled polycarbonate body which is machined or molded to form the cavity 22 as well as the opening 60 through which the wires 44–49 extend. The end of the housing 20 from which the wires extend is covered by an injection-molded polyurethane boot 64 which also seals the leading end of the sheath of cable 18 enclosing the wires 44–49. A stainless steel sleeve 68 is mounted on the housing 20 and extends over the leading edge of the polyurethane boot so as to reinforce the juncture between the polyurethane boot 64 and the housing 20 while also providing a durable member for securing the housing.

The radiation emitter 26 is an infrared emitting diode (IRED), for example TRW OP268FA generating peak radiant energy at 950 nm.

The light responsive cells 28, 30, 32 and 34 are solar cells, for example EG&G-VACTEC-VTS-3012.

The temperature sensor 40 is a solid state transducer, for example ANALOG DEVICES AD590.

The baffle 38 is a tube formed from an infrared opaque material, for example gold or stainless steel, which is corrosion resistant. The tubular baffle 38 extends perpendicular to the printed circuit board 24, is telescoped over the IRED 26, and has its upper end flush with the face of the epoxy fill 41 at the top of the cavity 22. The height and closeness of the walls of the baffle 38 above the IRED and sensors is selected to produce a desired minimum backscatter angle with a desired measurement volume. Greater heights increase the minimum backscatter angle, but decrease the measurement volume, while lesser heights decrease the minimum backscatter angle, but increase the measurement volume. A measurement volume of about 3 cc with a minimum backscatter angle of 140° is preferred.

Figure 4:
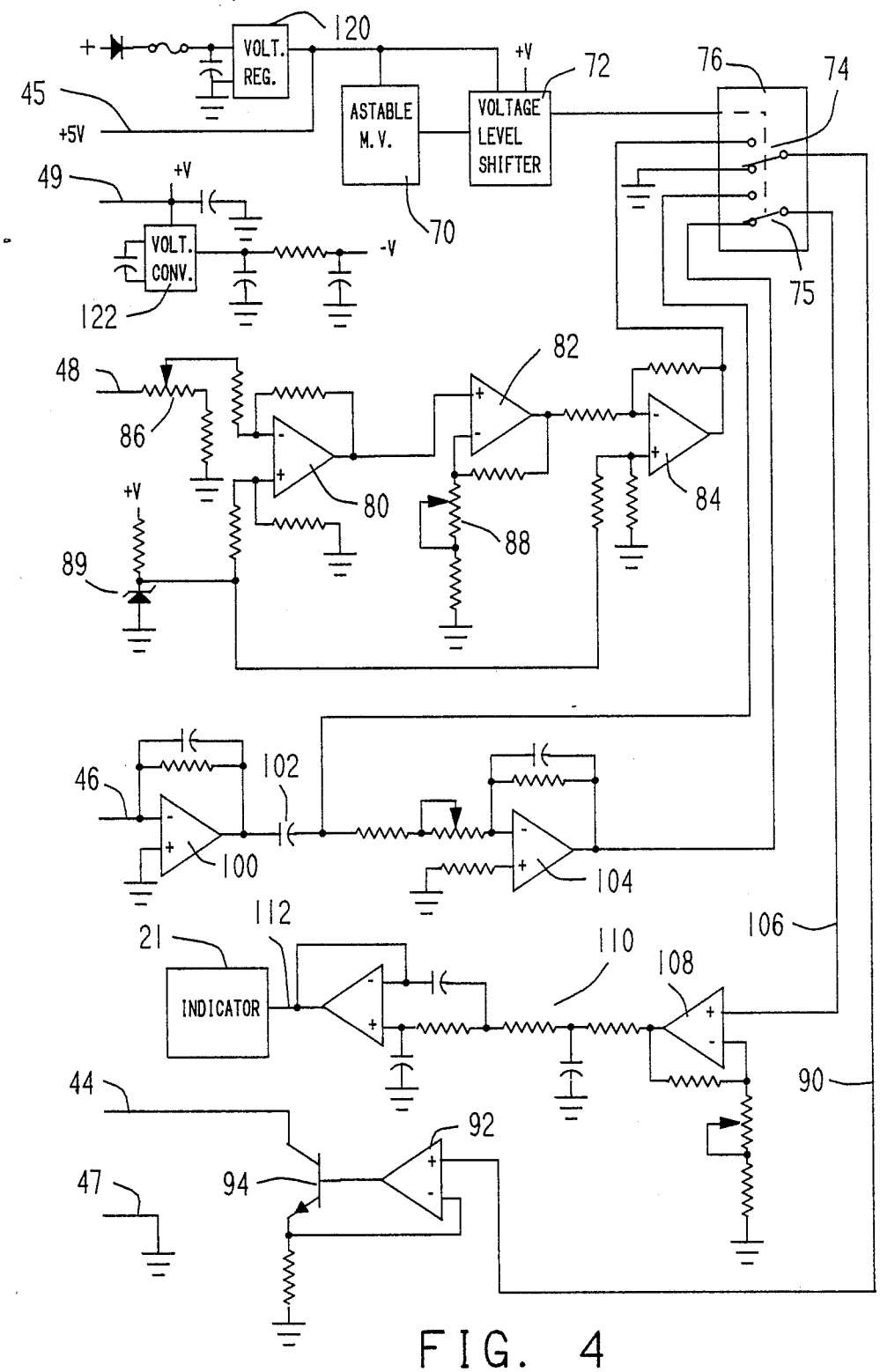
FIG. 4 is a schematic diagram of an electrical circuit for operating the sensor of FIGS. 1-3.
Figure 5:
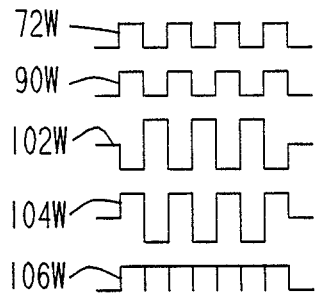
FIG. 5 is a waveform diagram showing waveforms of signals employed in the circuit of FIG. 4.

As shown in FIG. 4, the operating circuit includes a free-running or astable multivibrator 70 which generates a suitable AC signal, such as a 1 kHz square wave 72 W (FIG. 5), which is applied through voltage level shifter 72 to gating inputs of a pair of SPDT analog switches 74 and 75 in unit 76. One switch 75 in the unit 76 alternatively gates ground and a reference voltage for the voltage-controlled current source (VCCS) that drives IRED 26. This reference voltage is determined by the signal on line 48 from the temperature sensor 40 and which is applied through amplifiers 80, 82 and 84 to one input of the switch 74. The variable resistance 86 on the input of the differential amplifier 80 is used in nulling the output at the upper set point of the temperature compensation range. Amplifier 80 compares the input with a predetermined voltage from Zener diode 89 and outputs a temperature error voltage. Amplifier 82 with potentiometer 88 determine the gain of the temperature error voltage. Differential amplifier 84 is utilized to set the reference voltage level of the VCCS drive for the IRED. The resulting AC output 90 W (FIG. 5) on line 90 from switch 74 is applied to the VCCS formed by amplifier 92 operating transistor 94 to pulse the IRED 26 at the AC frequency over line 44. Since the magnitude of these pulses 90 W is controlled by the output of the temperature sensor, the output of the IRED 26 will vary in correspondence with changes in temperature. This cancels temperature-responsive changes in the output of the IRED as well as in the signal produced by the radiation sensors so as to eliminate the temperature variability of the optical sensor.

The output from the photodetector or radiation sensors on line 46 is applied through an amplifier 100 and DC isolating capacitance 102 to one input of the switch 75 in the unit 76 (waveform 102 W). An inverter unity amplifier 104 has one input connected to the output of the capacitance 102 and has its output (waveform 104 W) connected to the second input of the switch 75. The analog switch 75 driven by the square wave 72 W demodulates the AC component of the input signal which has the frequency of the astable multivibrator to generate an output (waveform 106 W) which is applied on line 106 to amplifier 108. This passes through a low pass filter 110 to output 112 which is then displayed by the indicator 21 such as an analog voltmeter or recorded by a data logger.

As an alternative to the control of the VCCS drive for the IRED by the output of the temperature sensor, the gain of sensor input could be controlled. For example, the amplifier 100 could be an amplifier controlled by a suitably scaled signal derived from the signal from the temperature sensor so as to eliminate temperature variability of the optical sensor.

The circuit of FIG. 4 also contains voltage regulator 120 and voltage converter 122 for generating voltages employed by the circuitry.

Figure 6:
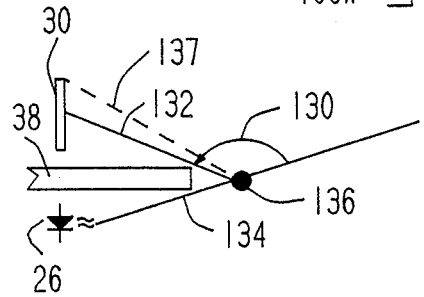
FIG. 6 is a diagram illustrating the scattering angle of detection for the sensor of FIGS. 2 and 3.

The backscattering angle 130, shown in FIG. 6, for the reflected radiation from a particle 136 is the angle that a reflected beam 132 makes with the emitted beam 134. Backscattering at large angles 130, greater than 140°, substantially eliminates sensing of scattered radiation from bubbles and translucent organic material since these materials do not reflect infrared light at these large angles. When particle 136 is at a minimum height over the sensor so as to reflect a ray 137 to the far edge of the cell 30 the ray 137 has a backscatter angle corresponding to the minimum backscatter angle.

Figure 7:
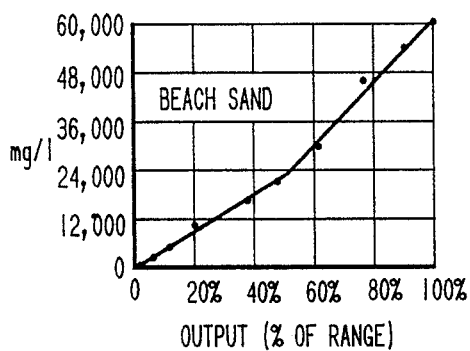
FIG. 7 is a graph of a sample calibration for determining concentration of beach sand in sea water relative to output for the turbidimeter of FIG. 1.
Figure 10:
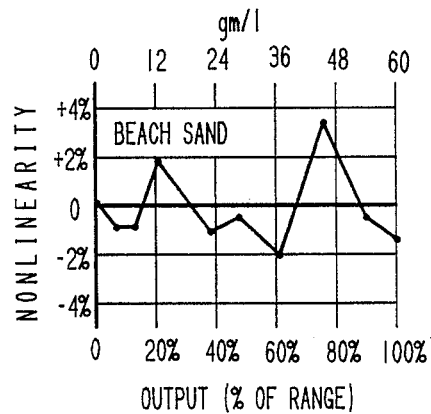
FIG. 10 is a graph showing the deviation of the calibration of FIG. 7 from a least square straight line with the deviation expressed as a percentage of the calibration range.
Figure 8:
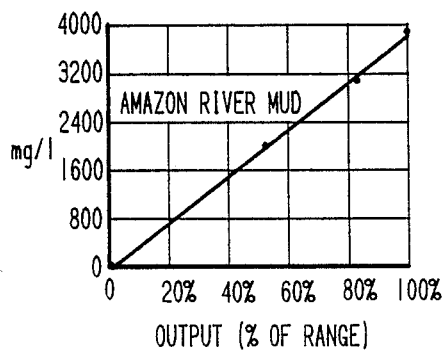
FIG. 8 is a calibration graph similar to FIG. 7 but of Amazon River mud.
Figure 11:
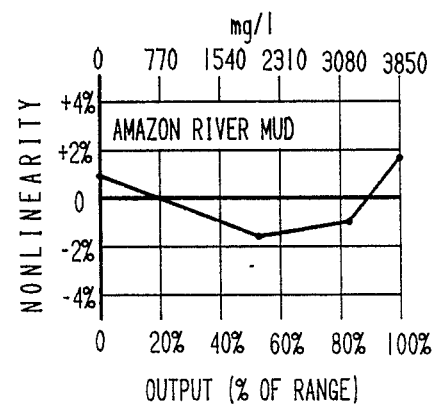
FIG. 11 is a graph similar to FIG. 10 but of Amazon River mud.
Figure 9:
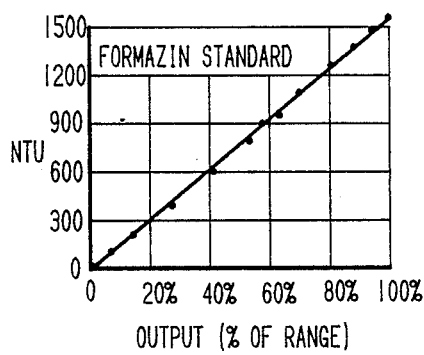
FIG. 9 is a graph of calibration performed using standard Formazin to calibrate output in nephelometric turbidity units (NTU)
Figure 12:
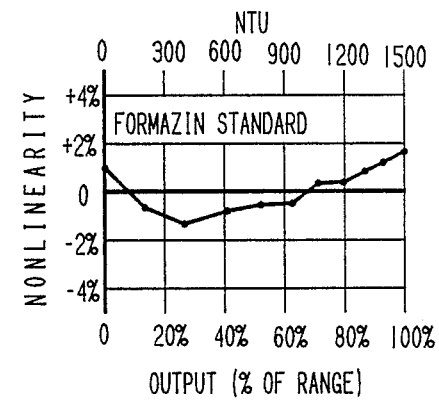
FIG. 12 is a graph similar to FIGS. 10 and 11 but of the Formazin standard of FIG. 9.

FIGS. 7, 8 and 9 illustrate sample calibrations of the units for beach sand, Amazon River mud and a Formazin standard. FIGS. 10, 11 and 12 illustrate deviations of the calibration data of FIGS. 7, 8 and 9, respectively, from a least square straight line expressed as a percentage of the calibration range.

The sensor illustrated in FIGS. 2 and 3 is a rugged pressure-resistant submersible probe which is relatively inexpensive to manufacture. The sensor is compact, hydrodynamically smooth to produce minimal disturbance of fluid flow and thus avoid spurious particle concentrations which can be produced by hydrodynamically rough probe shapes. The polycarbonate housing 20 is durable and wear-resistance while being light weight and easy to manufacture.

Having the IRED surrounded on four sides by sensor cells with a tubular baffly shielding the sensor cells from direct irradiation results in optimal maximization of the sensor area and the backscatter angle. A larger sensor area increases sensitivity and range, while a larger minumum backscatter angle decreases undesired backscatter from bubbles or biogenic material to further increase sensitivity to the particulate material being measured. Prior art sensors could not produce the combination of sensitivity with backscatter angle as is produced by the disclosed sensor.

The printed circuit board 24 enables efficient and reliable construction of the sensor. The emitter and sensing components on the printed circuit board can be assembled using efficient, cost effective printed circuit board assembly techniques. Additionally, the printed circuit board 24 provides for precise relative positioning of the components and holds the components in their relative positions during the epoxy potting. This reduces variations and failures in sensors compared to sensors having components which must be separately aligned and held in positions during encapsulation.

Having a temperature sensor mounted in the optical sensor and used to compensate the optical sensor operating circuit, eliminates variations in the output resulting from temperature variations of the fluid. Thus separate temperature measurements and corresponding adjustment of the resultse is not necessary.

Figure 13:
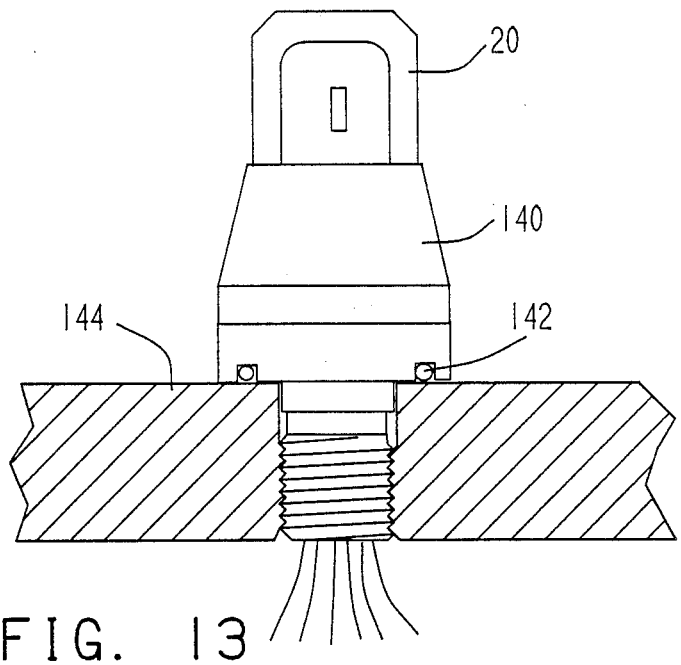
FIG. 13 is a sectional view of a modified sensor in accordance with the invention.

A modification is illustrated in FIG. 13 wherein the molded housing 20 is fastened to a threaded mounting structure 140 which has an O-ring seal 142 so that the sensor may be mounted in a bulkhead 144, an inside wall of a tank, or the like.

Figure 14:
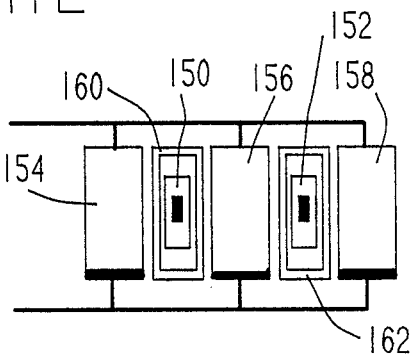
FIG. 14 is a plan view showing a modified arrangement of radiation emitters and radiation sensors in accordance with the invention.

FIG. 14 illustrates a modification of the arrangement of IRED and radiation sensors, and particularly provides for a series of two IREDS 150 and 152 which are interdigitally interspersed between series arranged radiation sensing cells 154, 156 and 158. Tubular infrared opaque baffles 160 and 162 prevent radiation from the IREDs from directly impinging on the sensors. This arrangement produces an overall increase in sensitivity, for example 50%, but is more costly and less reliable than the embodiment of FIG. 1 due to a higher parts count and nonlinear aging of the radiant outputs of the IREDs.

Since many modifications, variations and changes in detail may be made to the above-described embodiments without departing from the scope and spirit of the invention, it is intended that all matter in the foregoing description, and shown in the accompanying drawings be interpreted as illustrative and not in a limiting sense.

What is claimed is:

1. An apparatus for measuring particle concentration in fluids comprising
    a housing having a cavity defining an opening for facing a fluid,
    a printed circuit board adjacent the cavity,
    a radiation emitting diode mounted on the printed circuit board for projecting radiation from the opening into the fluid;
    a plurality of radiation detectors mounted on the printed circuit board adjacent the diode and on at least two different sides of the radiation emitting diode for receiving radiation passing from the fluild into the opening;
    means for preventing radiation emitted by the diode from impinging directly on the detectors such that the detectors respond to radiation reflected by particles in the fluid;
    a potting matereial which is transparent to the radiation emitted by the diode, filling the cavity and encasing the printed circuit board, the diode and the detectors; and
    wire means connected to the printed circuit board and extending from the housing for connecting the diode and the detectors to a particle sensor operating and indicating circuit.

2. An apparatus as defined in claim 1 including a temperature sensor mounted on the printed circuit board and encapsulated in the potting material.

3. An apparatus as claimed in claim 1 wherein the radiation emitting diode is an infrared emitting diode and the plurality of radiation detectors are solar cells.

4. An apparatus as claimed in claim 3 wherein the plurality of radiation detectors include four cells mounted on the four sides of the radiation emitting diode.

5. An apparatus as claimed in claim 1 wherein the housing is formed from glass-filled polycarbonate.

6. An apparatus as claimed in claim 1 wherein the printed circuit board is perpendicular to a line passing through opening of the cavity.

7. An apparatus as claimed in claim 1 wherein the preventing means includes a tubular baffle telescoped over the radiation emitting diode and extending to a surface of the potting material in the opening of the cavity.

8. An apparatus as claimed in claim 7 wherein the plurality of radiation detectors include four cells mounted on the four sides of the radiation emitting diode, and the size and spacing of the detectors and the height of the tubular baffle are selected to produce a measurement volume of about three cubic centimeters and a maximum detector area with a minimum backscatter angle of 140°.

9. An apparatus for measuring particle concentration in fluids. comprising
 a housing having a cavity defining an opening for facing a fluid;
 a radiation emitting diode in the cavity;
 a plurality of radiation detectors in the cavity adjacent the diode and on at least two different sides of the infrared emitting diode;
 means for preventing radiation emitted by the diode from impinging directly on the detectors such that the detectors receive radiation reflected by particles in the fluid;
 a temperature sensor in the cavity;
 a potting material, which is transparent to the radiation emitted by the diode, filling the cavity and encasing the diode, the detectors and the temperature sensor;
 means for energizing the diode to project radiation into the fluid;
 means responsive to electrical signals generated by the radiation detectors for indicating a particle concentration; and
 means responsive to electrical signals from the temperature sensor for varying the diode energizing means or the indicating means to eliminate temperature variation of the indicated particle concentration.

10. An apparatus as claimed in claim 9 wherein the varying means varies the magnitude of the current energizing the radiation emitting diode.

11. An apparatus as claimed in claim 10 wherein the diode energizing means includes means for energizing the diode with a square wave current, the varying means varies the magnitude of the square wave current; and the particle concentration indicating means includes means for detecting a square wave signal from the radiation detectors to produce a signal indicating particle concentration.

12. An apparatus as claimed in claim 11 including oscillator means for generating a clock signal; and wherein the varying means includes means for generating a variable reference voltage which varies in correspondence with changes in temperature in a fluid being measured; and the diode square wave energizing means includes double-throw switch means operated by the clock signal for alternating the variable reference voltage and a ground voltage, and a voltage controlled current source having an input connected to an output of the switch means for energizing the diode.

13. An apparatus as claimed in claim 12 wherein the square wave detecting means includes a series capacitance for passing the square wave component of the signal from the radiation detectors, a unity inverting amplifier connected to the capacitance for generating an inverted square wave component, and a second double-throw switch means operated by the clock signal and having two inputs receiving the square wave components and inverted square wave component to generate the particle concentration indicating signal.

* * * * *